United States Patent
Nagashima et al.

(10) Patent No.: US 6,794,531 B2
(45) Date of Patent: Sep. 21, 2004

(54) PROCESS FOR PRODUCTION OF ASPARTYL DIPEPTIDE ESTER DERIVATIVE, NOVEL PRODUCTION INTERMEDIATE THEREFOR, AND PROCESS FOR PRODUCTION THEREOF

(75) Inventors: Kazutaka Nagashima, Kawasaki (JP); Yuuichi Aoki, Kawasaki (JP); Tadashi Takemoto, Kawasaki (JP); Yusuke Amino, Kawasaki (JP); Nao Funakoshi, Kawasaki (JP); Eriko Ono, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/117,196

(22) Filed: Apr. 8, 2002

(65) Prior Publication Data

US 2002/0133037 A1 Sep. 19, 2002

Related U.S. Application Data

(63) Continuation of application No. PCT/JP00/06626, filed on Sep. 26, 2000.

(30) Foreign Application Priority Data

Oct. 7, 1999 (JP) .......................................... 11-287398
Dec. 27, 1999 (JP) .......................................... 11-371284

(51) Int. Cl.$^7$ .............................................. C07C 229/00
(52) U.S. Cl. .............................. 560/40; 560/37; 560/41
(58) Field of Search ............................... 560/37, 40, 41

(56) References Cited

U.S. PATENT DOCUMENTS

| 4,486,607 | A | * | 12/1984 | Webb |
| 5,480,668 | A |   | 1/1996 | Nofre et al. |
| 5,728,862 | A | * | 3/1998 | Prakash |

FOREIGN PATENT DOCUMENTS

| EP | 1 070 726 | 1/2001 |
| EP | 1 088 829 | 4/2001 |
| EP | 1114 828 | 7/2001 |
| FR | 269784 | 5/1994 |
| WO | 99/52937 | 10/1999 |
| WO | 00/00508 | 1/2000 |
| WO | 00/17230 | 3/2000 |

OTHER PUBLICATIONS

Chemistry Letters 1998, 11, pp. 1143–1144.
Engelhard Industries Technical Bulletin, vol. IV, No. 2, 1963, pp. 49–51.
J. Org. Chem., vol. 59, No. 9, 1994, pp. 2304–2313.

* cited by examiner

*Primary Examiner*—Johann Richter
*Assistant Examiner*—Paul A. Zucker
(74) *Attorney, Agent, or Firm*—Oblon, Spivak, McClelland, Maier & Neustadt, P.C.

(57) ABSTRACT

The present invention relates to a method of manufacturing aspartyl dipeptide ester compounds, which can be used as sweeteners, and aldehydes that can be used in the manufacturing processes.

20 Claims, No Drawings

PROCESS FOR PRODUCTION OF ASPARTYL DIPEPTIDE ESTER DERIVATIVE, NOVEL PRODUCTION INTERMEDIATE THEREFOR, AND PROCESS FOR PRODUCTION THEREOF

CROSS-REFERENCE TO A RELATED APPLICATION

The present application is a continuation application of PCT/JP00/06626 filed Sep. 26, 2000, the entire contents of which is incorporated by reference.

BACKGROUND OF THE INVENTION

1. Field of the Invention

The present invention relates to a novel process for production of an aspartyl dipeptide ester derivative that be used as a sweetener. Furthermore, the present invention relates to a process for production of a arylpropionaldehyde, which can be used to produce a N-[N-[3-(3-hydroxy-4-methoxyphenyl) propyl]-L-α-aspartyl]-L-phenylalanine 1-methyl ester.

2. Discussion of the Background

In recent years, as eating habits have increased, excessive weight gain and obesity caused by excessive sugar intake has been more frequently observed. Additionally, diseases accompanied by such weight gain and obesity are becoming more prevalent. Accordingly, the development of a low-calorie sweetener (sweetening agent) that replaces sugar has been strongly in demand. Aspartame is widely used as a sugar substitute or sweetener; and is excellent in safety and sweetening quality. However, a drawback of aspartame is that is somewhat unstable.

The present inventors have found the compound of formula (3) can be used as a sweetener and is excellent in stability. Moreover, this compound of formula (3) has a greater sweetening potency and therefore, has an advantage in cost per a sweet taste. However, an efficient method for manufacturing this process has not been previously described.

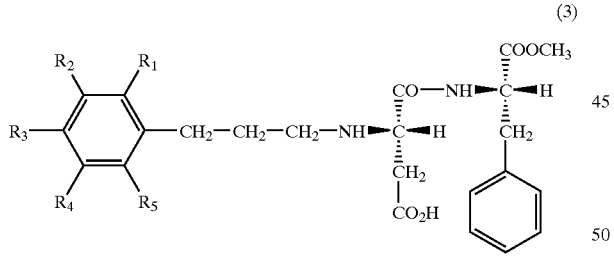

(3)

In formula (3), $R_1$, $R_2$, $R_3$, $R_4$ and $R_5$ are independently selected from the group consisting of a hydrogen atom, a hydroxyl group, an alkoxy group having 1 to 3 carbon atoms, an alkyl group having 1 to 3 carbon atoms, and a hydroxyalkyloxy group having 2 or 3 carbon atoms, wherein two symbols of $R_1$ and $R_2$, or two symbols of $R_2$ and $R_3$ may be combined together to denote a methylenedioxy group.

N-[N-(3-phenylpropyl)-L-α-aspartyl]-L-phenylalanine 1-methyl ester and N-[N-[3-(3-methoxy-4-hydroxyphenyl) propyl)-L-α-aspartyl]-L-phenylalanine 1-methyl ester, which are described in WO94/11391, are poor sweeteners compared to the compounds of formula (3) described herein. However, WO94/11391 does not provide an example that shows a suitable operation for the synthesis and certain starting material employed as well.

For example, to produce 3-hydroxy-4-methoxyphenyl derivative a β-O-benzyl-α-L-aspartyl-L-phenylalanine methyl ester is reductively alkylated with 3-benzyloxy-4-methoxycinnamaldehyde and NaB(OAc)$_3$H, followed by the removal of the benzyl group of a protecting group was employed. However, 3-benzyloxy-4-methoxycinnamaldehyde used for the process is synthesized in a reaction that requires four reaction steps from the starting material 3-hydroxy-4-methoxycinnamic acid, as shown in the following reaction process 1. Therefore, this reaction process does not provide an industrial profitable means to produce the compounds. Likewise, a production process for N-[N-[3-(3-hydroxy-4-methoxyphenyl) propyl]-L-α-aspartyl]-L-phenylalanine 1-methyl ester that uses the aldehyde described above as the starting material is to not an industrially profitable process, because in addition to the reductive alkylation, a deprotection reaction is required.

Reaction Process 1

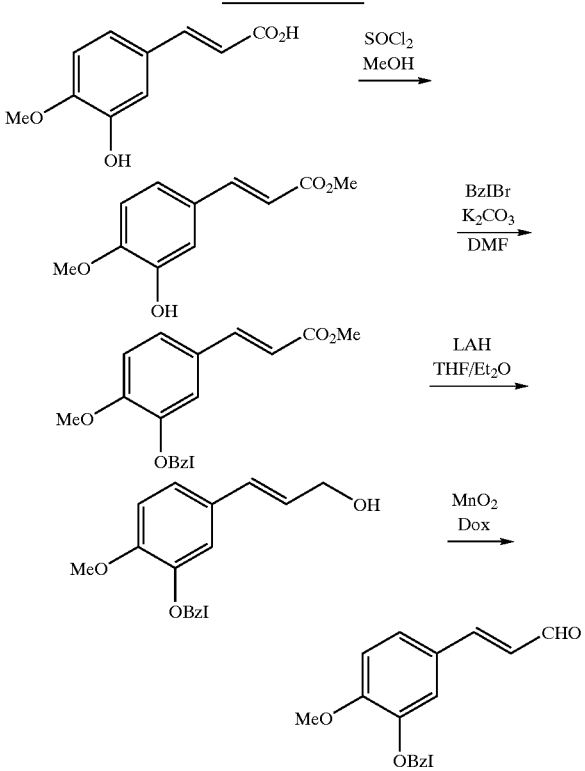

Therefore, development of an efficient and industrial process for producing an aspartyl dipeptide ester derivative represented by the general formula (3) described above, in particular, N-[N-[3-(3-hydroxy-4-methoxyphenyl) propyl]-L-α-aspartyl]-L-phenylalanine 1-methyl ester is needed.

SUMMARY OF THE INVENTION

Accordingly, the present invention provides an efficient and industrial process for producing an aspartyl dipeptide ester derivative represented by the general formula (3), which can be used as a sweetener.

Another object of the present invention is to provide an efficient and industrial process for producing an aldehyde represented by the following general formula (1) or (2), which can serve is intermediates for producing the aspartyl dipeptide ester derivative described above.

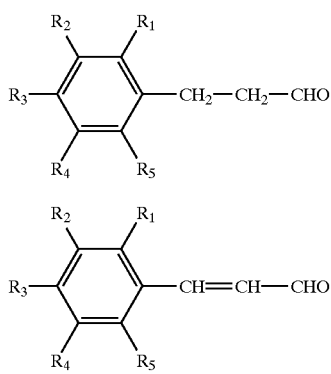

wherein $R_1$, $R_2$, $R_3$, $R_4$ and $R_5$ are independently selected from a hydrogen atom, a hydroxyl group, an alkoxy group having 1 to 3 carbon atoms, an alkyl group having 1 to 3 carbon atoms, a benzyloxy group and a hydroxyalkyloxy group having 2 or 3 carbon atoms, wherein two symbols of $R_1$ and $R_2$, or two symbols of $R_2$ and $R_3$ may be combined together to denote a methylenedioxy group.

Another object of the present invention is to provide novel intermediate 3-(3-hydroxy-4-methoxyphenyl) propionaldehyde.

DETAILED DESCRIPTION OF THE INVENTION

The present inventors have discovered an efficient process for producing the compounds represented by the above general formula (3), and as a result, have found that an aspartyl dipeptide ester derivative can be produced easily through reductive alkylation of an aspartame, in the presence of a catalyst and hydrogen, with an aldehyde of formulas (1) or (2).

In addition, the present inventors have found that the aldehyde represented by formulas (1) or (2) is an excellent intermediate for producing the aspartyl dipeptide ester derivative and have also found industrial efficient processes to produce these aldehydes.

The hydrocinnamaldehyde derivative can be obtained in a process where a cinnamic acid derivative is subjected to reaction conditions suitable for selectively reducing a carbon—carbon double bond therein, which reaction is conducted preferably in the presence of the hydrogenation catalyst (hydrogen addition) to obtain a hydrocinnamic acid derivative. Subsequently, a carboxyl group is reduced to a formyl group, preferably the reduction is performed in the presence of a catalyst.

A hydrocinnamaldehyde derivative can be obtained by a process where a carboxyl group in the cinnamic acid derivative is reduced to a formyl group, preferably in the presence of a catalyst, which yields a cinnamaldehyde derivative. Subsequently a carbon—carbon double bond is selectively reduced in the cinnamaldehyde derivative, preferably in the presence of a hydrogenation catalyst (hydrogen addition).

For example, N-[N-[3-(3-hydroxy-4-methoxyphenyl) propyl]-L-α-aspartyl]-L-phenylalanine 1-methyl ester, which provides high sweetening potency, may be prepared from 3-(3-hydroxy-4-methoxyphenyl) propionaldehyde thereby providing an industrially efficient process as depicted in the following reaction process 2.

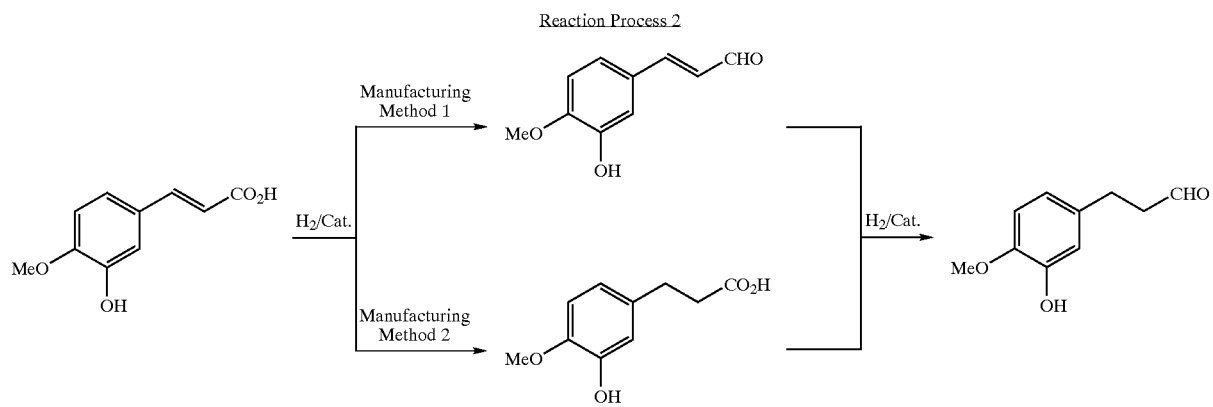

Reaction Process 2

Processes for Producing Aspartyl Dipeptide Ester Derivative

To produce an aspartyl dipeptide ester derivative represented by the following general formula (3) an aspartame can be reductively alkylated with an aldehyde represented by the following general formula (1) or formula (2), in the presence of hydrogen and a catalyst:

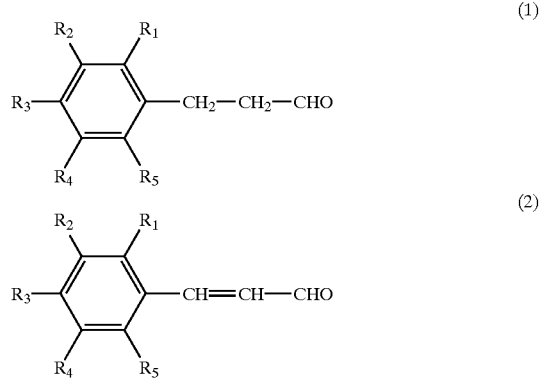

In the these formula, $R_1$, $R_2$, $R_3$, $R_4$ and $R_5$ are independently a hydrogen atom, a hydroxyl group, an alkoxy group having 1 to 3 carbon atoms, an alkyl group having 1 to 3 carbon atoms, and a hydroxyalkyloxy group having 2 or 3 carbon atoms. In one embodiment, $R_1$ and $R_2$, or $R_2$ and $R_3$ may be combined together to denote a methylenedioxy group.

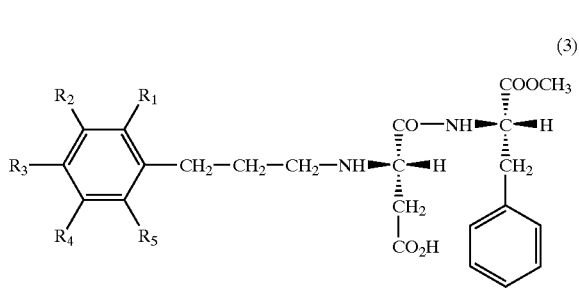

(3)

In the formula (3), $R_1$, $R_2$, $R_3$, $R_4$ and $R_5$ are independently a hydrogen atom, a hydroxyl group, an alkoxy group having 1 to 3 carbon atoms, an alkyl group having 1 to 3 carbon atoms, and a hydroxyalkyloxy group having 2 or 3 carbon atoms. In one embodiment $R_1$ and $R_2$, or $R_2$ and $R_3$ may be combined together to denote a methylenedioxy group.

In the reductive alkylation reaction of the present invention, where $R_1$ to $R_5$ is a hydroxyl group, the hydroxyl group may be protected with a benzyl group, for example, $R_1$ to $R_5$ may be independently a benzyloxy group. In this case, the benzyl group may be removed (benzyl group-removing reaction) in the benzyloxy moiety, where the protected hydroxyl group may be converted into a hydroxyl group, and the compound of formula (3) obtained.

Processes for Producing Cinnamaldehyde Derivative and the Hydrocinnamaldehyde

The carboxyl group in the cinnamic acid derivative represented by formula (4) is partially reduced into a formyl group, preferably in the presence of a catalyst, to obtain the cinnamaldehyde derivative represented by formula (2). Subsequently, the carbon—carbon double bond therein is selectively reduced, preferably in the presence of a hydrogenation catalyst whereby the hydrocinnamaldehyde derivative represented by formula (1) is obtained.

Further, in the cinnamic acid derivative represented by formula (4), the carbon—carbon double bond therein is selectively reduced, preferably in the presence of a hydrogenation catalyst to obtain the hydrocinnamic acid derivative represented by formula (5). Subsequently, the carboxyl group therein is partially reduced, preferably in the presence of a catalyst, into a formyl group, whereby the hydrocinnamaldehyde derivative represented by formula (1) is obtained.

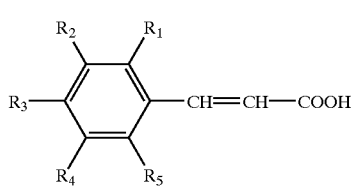

(4)

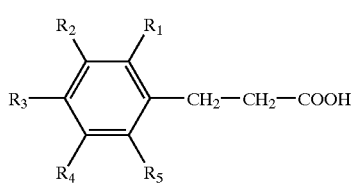

(5)

In the above formulas, $R_1$, $R_2$, $R_3$, $R_4$ and $R_5$ are independently a hydrogen atom, a hydroxyl group, an alkoxy group having 1 to 3 carbon atoms, an alkyl group having 1 to 3 carbon atoms, and a hydroxyalkyloxy group having 2 or 3 carbon atoms. In one embodiment $R_1$ and $R_2$, or $R_2$ and $R_3$ may be combined together to form a methylenedioxy group.

Hydrocinnamaldehyde Derivatives (Arylpropionaldehyde), Process for Production thereof, and Uses Thereof To prepare a 3-(3-hydroxy-4-methoxyphenyl) propionaldehyde, a 3-hydroxy-4-methoxycinnamaldehyde may be subjected to reaction conditions to selectively reduce a carbon—carbon double bond; or a 3-(3-hydroxy-4-methoxyphenyl) propionic acid may be subjected to reaction conditions to convert a carboxyl group into a formyl group. In a preferred embodiment the 3-hydroxy-4-methoxycinnamaldehyde is obtained through a process by converting a carboxy group in a 3-hydroxy-4-methoxycinnamic acid into a formyl group. The conversion of a carboxy group into a formyl group is preferably accomplished by partially reducing the carboxyl group. In a preferred embodiment the 3-(3-hydroxy-4-methoxyphenyl) propionic acid is obtained by a process where a carbon—carbon double bond in 3-hydroxy-4-methoxycinnamic acid is selectively reduced, more preferably the carbon—carbon double bond is selectively reduced in the presence of hydrogenation a catalyst, and most preferably the hydrogenation catalyst is at least one of palladium, platinum and/or rhodium based catalysts.

To produce a N-[N-[3-(3-hydroxy-4-methoxyphenyl) propyl]-L-α-aspartyl]-L-phenylalanine 1-methyl ester the above processes can be extended to include a step of reductive alkylation of the arylpropionaldehyde with an aspartame.

In the process for producing an aspartyl dipeptide ester, to a solution which has dissolved or suspended aspartame, the aldehyde is dissolved, a catalyst is added, and is stirred under a hydrogen gas atmosphere. After completion of the reaction, the catalyst may be removed by filtration, and the filtrate is concentrated to obtain the aspartyl dipeptide ester derivative. This derivative may be subjected to purification using chromatography or the like.

There is no particular limitation to the solvent to be employed in the reaction provided it is an inactive material to the starting material for the reaction, the catalyst and the product. The solvent to dissolve aspartame and the aldehyde may be a homogenous solvent consisting of one kind of organic solvent only; a mixed solvent consisted of two or more organic solvents, or a mixture of one ore more organic solvents with water may be employed. Preferred solvents include, for example, methanol, ethanol, tetrahydrofuran, acetonitrile and dimethylformamide. Most preferred a methanol or a water-containing methanol solvents.

Suitable hydrogenation catalyst include, but are not limited to as palladium based catalyst (palladium carbon and the like), platinum based catalyst (platinum carbon and the like), and rhodium based catalyst. Preferred catalysts are palladium carbon and platinum carbon.

The reductive alkylation reaction can be conducted by hydrogenation (hydrogen addition), preferably under hydrogen pressure, which is preferably from about 0.1 to about 1.0 MPa.

The temperature for the reactions is not limited provided it is selected to be suitable for the reductive alkylation reaction. In order to suppress a secondary reaction and to promote the reaction desired, preferred temperature ranges are from about 15 to about 50° C., for reaction time of from about 2 to about 72 hours.

The molar ratio of aspartame to the aldehyde can be employed preferably from about 0.5 to about 1.5 moles of aspartame per 1 mole of the aldehyde.

To produce the aspartyl dipeptide ester derivative by way of the reductive alkylation reaction, in one embodiment $R_2$ is a hydroxyl group, $R_3$ is a methoxy group, and $R_1$, $R_4$ and $R_5$ are a hydrogen atom in the above formulas (1)–(3), and in the formulae (1) and (2), $R_2$ may be a benzyloxy group. In another embodiment $R_2$ is a methyl group, $R_3$ is a hydroxyl group, and $R_1$, $R_4$ and $R_5$ are hydrogen atoms in formulas (1)–(3), and in the formulas (1) and (2), $R_3$ may be a benzyloxy group. In another embodiment $R_2$ and $R_3$ are combined together to denote a methylenedioxy group, and $R_1$, $R_4$ and $R_5$ are hydrogen atoms in formulas (1)–(3). In another embodiment $R_1$ is a hydroxyl group, $R_3$ is a methoxy group, and $R_2$, $R_4$ and $R_5$ are hydrogen atoms in the formulas (1)–(3), and in the formulas (1) and (2), $R_1$ may be a benzyloxy group. In another embodiment $R_3$ is a hydroxyl group, and $R_1$, $R_2$, $R_4$ and $R_5$ are hydrogen atoms in formulas (1)–(3), and in the formulas (1) and (2), $R_3$ may be a benzyloxy group. In another embodiment $R_2$ is a hydroxyl group, $R_3$ is a methyl group, and $R_1$, $R_4$ and $R_5$ are hydrogen atoms in formulas (1)–(3), and in the formulas (1) and (2), $R_2$ may be a benzyloxy group. In another embodiment $R_1$ and $R_3$ are a hydroxyl group, and $R_2$, $R_4$ and $R_5$ are hydrogen atoms in formulas (1)–(3), and in the formulas (1) and (2), $R_1$ and/or $R_3$ may be a benzyloxy group.

Processes for Producing Cinnamaldehyde Derivatives and Hydrocinnamaldehyde Derivatives To produce the cinnamaldehyde derivative and the hydrocinnamaldehyde derivative a manufacturing method 1 depicted below may be employed. In this method the carboxyl group of the cinnamic acid derivative of formula (4) is partially reduced, preferably in the presence of a catalyst. Subsequently, the carboxyl group is converted into a formyl group to yield the cinnamaldehyde derivative of formula (2). The carbon—carbon double bond then is selectively reduced, preferably in the presence of a hydrogenation catalyst, yielding the hydrocinnamaldehyde derivative of formula (1).

In another embodiment, as shown in the following manufacturing method 2 a carbon—carbon double bond of the cinnamic acid derivative of formula (4) is selectively reduced, preferably in the presence of a hydrogenation catalyst yielding a hydrocinnamic acid derivative of formula (5). Subsequently, the carboxyl group is partially reduced, preferably in the presence of a catalyst, into a formyl group, yielding the hydrocinnamaldehyde derivative of formula (1).

In the manufacturing method 1, for example, to produce 3-hydroxy-4-methoxycinnamaldehyde from 3-hydroxy-4-methoxycinnamic acid, the 3-hydroxy-4-methoxycinnamic acid may be partially reduced, using methods known in the art, for example, as described in Chem. Lett., 1998, 11, 1143. This process includes the step of reducing the 3-hydroxy-4-methoxycinnamic acid with hydrogen in an organic solvent and in the presence of pivalic acid anhydride, palladium based compounds (such as palladium acetate), and triphenylphosphine derivatives (triarylphosphine and the like). There is no particular limitation to the solvent to be employed in the reaction provided it is an inactive material to the starting material for the reaction, the catalyst and the product. Preferably, acetone, tetrahydrofuran, and the like are employed. The amount of pivalic acid anhydride used in the reaction is preferably an equimolar amount or more of pivalic acid anhydride relative to the 3-hydroxy-4-methoxycinnamic acid. For example, from about 1 to about 5 times moles of pivalic acid anhydride to the 3-hydroxy-4-methoxycinnamic acid may be used.

Triphenylphosphine derivative useful include, but are not limited to triphenylphosphine, and tritolylphosphine. The catalyst(s), for example, palladium acetate and triphenylphosphine derivative are employed in varying molar percentages.

The temperature for reaction may be conducted at any temperature, but at higher reaction temperature, the reaction may proceed faster and therefore completed in a shorter time.

To produce the 3-(3-hydroxy-4-methoxyphenyl) propionaldehyde from the 3-hydroxy-4-methoxycinnamaldehyde obtained in the above reaction, the carbon—carbon double bond in the 3-hydroxy-4-methoxycinnamaldehyde may be selectively reduced, preferably in the presence of the hydrogenation catalyst. More preferably, the carbon—carbon double bond is selectively reduced using methods known in the art, for example, as described in Engelhard. Ind. Tech. Bull., 1963, 4, 49. This process comprises the step of selectively reducing the 3-hydroxy-4-methoxycinnamaldehyde, in particular the carbon—carbon double bond therein with hydrogen in an organic solvent, for example, in the presence of the catalyst, which includes, for

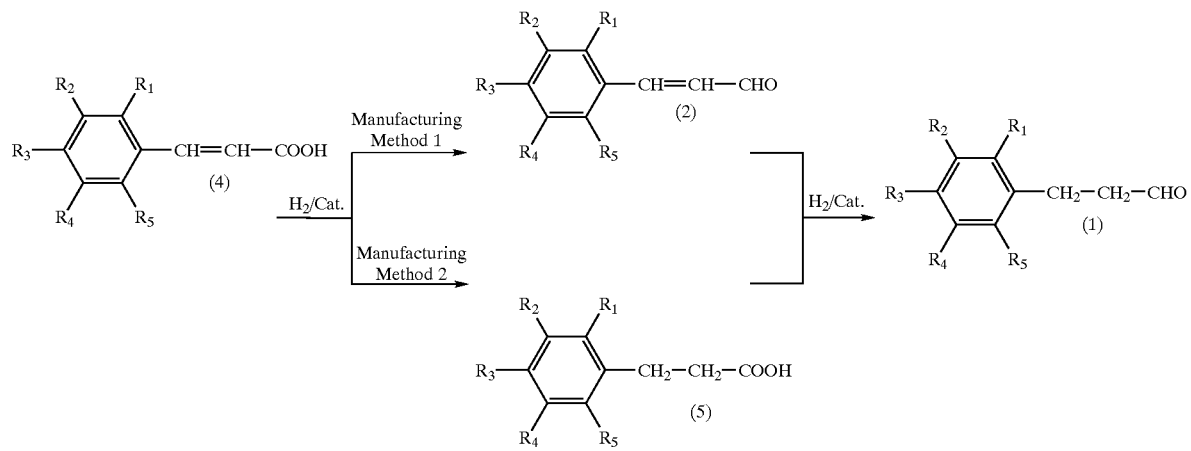

In the manufacturing method 2, preferably 3-hydroxy-4-methoxycinnamic acid is the cinnamic acid derivative of formula (4).

example, palladium based catalysts (such as palladium-alumina, palladium-calcium carbonate and the like), platinum based catalysts (such as platinum carbon and the like), rhodium based catalysts (such as rhodium-alumina and the like), or nickel based catalysts (such as nickel-formic acid and the like).

There is no particular limitation to the solvent to be employed in the reaction provided it is an inactive material to the starting material for the reaction (3-hydroxy-4-methoxycinnamaldehyde), the catalyst and the product (3-(3-hydroxy-4-methoxyphenyl) propionaldehyde). Preferably, the solvent is a lower alcohol such as methanol, ethanol and the like, tetrahydrofuran, and the like; more preferably, a lower alcohol may be employed, and most preferably methanol may be employed.

The catalyst may be a generic and conventional hydrogenation catalyst, such as palladium based catalysts (palladium-alumina, palladium-calcium carbonate and the like), platinum based catalysts (platinum carbon and the like), and rhodium based catalyst s(rhodium-alumina and the like), or nickel based catalysts (nickel-formic acid and the like). The catalyst may be used in any amount. For example, in case of 5% palladium-alumina, it may be preferably employed within a range of weight ratio of about one hundredth (1/100) to about one third (1/3) relative to the 3-hydroxy-4-methoxycinnamaldehyde. The reaction can be conducted by hydrogenation (hydrogen addition), preferably at a pressure of 0.1 MPa, and more preferable under hydrogen pressure of from about 0.1 to about 5.0 MPa.

The temperature for the reaction temperature is preferably from about 10 to about 30° C. However, to improve the solubility of the starting material or the object product, and also to improve the speed of the reaction, preferably the reaction solution may be heated up to about 60° C., more preferably from about 20 to about 50° C. The reaction may also be conducted at this temperature. The reaction may proceed for any amount of time, but preferably the reaction proceeds for about 2 to about 48 hours.

In the manufacturing method 2, for example, to produce 3-(3-hydroxy-4-methoxyphenyl) propionic acid from 3-hydroxy-4-methoxycinnamic acid, the carbon—carbon double bond may be selectively reduced in 3-hydroxy-4-methoxycinnamic acid. Preferably, the selective reduction is conducted using known process, for example, as described in J. Org. Chem., 1994, 59, 2304. This process comprises the step of selectively reducing the 3-hydroxy-4-methoxycinnamic acid, in particular the carbon—carbon double bond therein with hydrogen in an organic solvent. Preferably, the reaction is conducted in the presence of a catalyst. Preferred catalysts, include palladium based catalysts (such as palladium carbon, palladium-alumina and the like), platinum based catalysts (such as platinum carbon and the like), rhodium based catalysts (such as rhodium-alumina and the like), or nickel based catalysts (such as Raney Nickel and the like).

There is no particular limitation to the solvent to be employed in the reaction provided it is an inactive material to the starting material for the reaction (3-hydroxy-4-methoxycinnamic acid), the catalyst and the product (3-(3-hydroxy-4-methoxyphenyl) propionic acid). Preferably, a lower alcohol such as methanol, ethanol and the like, tetrahydrofuran, and a mixed solvent of such organic solvent (s) with water, and the like can be used. More preferably, a lower alcohol may be employed, for example, methanol and most preferred is a mixed solvent of methanol and water.

If a catalyst is used in the reaction, a generic and conventional hydrogenation catalyst may be used. For example, palladium based catalysts (palladium carbon, palladium-alumina and the like), platinum based catalysts (platinum carbon and the like), and rhodium based catalysts (rhodium-alumina and the like), or nickel based catalysts (Raney Nickel and the like), can be used.

The catalyst can be used in any amount but, for example, in case of 10% palladium carbon in the water content of 50%, the catalyst may be preferably employed within a range of weight ratio of about one hundredth (1/100) to about one third (1/3) relative to the 3-hydroxy-4-methoxycinnamic acid. The hydrogenation (hydrogen addition) is preferably carried out at a pressure of about 0.1 Mpa, and more preferably under hydrogen pressure of about 0.1 to about 1.0 MPa. The reaction temperature is preferably from about 10 to about 30. However, to improve the solubility of the starting material or the object product, and further to improve a reaction speed, the reaction solution may be heated up to about 60° C., preferably from about 30 to about 50° C. The can also be conducted at the preferred temperature. The reaction may proceed for any length of time, but preferred is a reaction time of about 2 to about 48 hours.

To produce a 3-(3-hydroxy-4-methoxyphenyl) propionaldehyde from the 3-(3-hydroxy-4-methoxyphenyl) propionic acid obtained in the above reaction, the 3-(3-hydroxy-4-methoxyphenyl) propionic acid may be directly partially reduced.

To produce an aspartyl dipeptide ester derivative, preferably a N-[N-[3-(3-hydroxy-4-methoxyphenyl) propyl]-L-α-aspartyl]-L-phenylalanine 1-methyl ester, from the cinnamaldehyde derivative or the hydrocinnamaldehyde derivative, preferably form the 3-(3-hydroxy-4-methoxyphenyl) propionaldehyde, the process may be conducted as explained in the process for production of the aspartyl dipeptide ester derivative, described above. Particularly, the aldehyde derivative obtained is reductively alkylated with an α-L-aspartyl-L-phenylalanine methyl ester (aspartame) under a condition for hydrogenation (hydrogen addition). The solvent that can be used should dissolve the starting materials, for example, alcohol, water-containing alcohol or the like may be used. The catalyst for hydrogenation is as described above, under the pressure, temperature and time conditions described herein.

The catalyst can be removed from the reaction after the aspartyl dipeptide ester derivative is prepared and the aspartyl didpeptide ester can be further purified yielding a sweetener having a high sweetening potency. For example, in case of N-[N-[3-(3-hydroxy-4-methoxyphenyl) propyl]-L-α-aspartyl]-L-phenylalanine 1-methyl ester, after the catalyst is removed, the solvent is removed by distillation, yielding a residue that may be subjected to a purification with a silica gel chromatography (for example, eluting solvent: ethyl acetate/methanol/chloroform=3/3/2). The eluted fractions containing the object compound, are concentrated under reduced pressure to yield N-[N-[3-(3-hydroxy-4-methoxyphenyl) propyl]-L-α-aspartyl]-L-phenylalanine 1-methyl ester in the solid form.

The following Examples provide an illustration of embodiments of the invention and should not be construed to limit the scope of the invention, which is set forth in the appended claims. In the following Examples, all methods described are conventional unless otherwise specified.

EXAMPLES

Example 1

Production of N-[N-[3-(3-Hydroxy-4-Methoxyphenyl) Propyl]-L-α-Aspartyl]-L-Phenylalanine 1-Methyl Ester Aspartame (5.89 g, 20.0 mmol) and 3-(3-hydroxy-4-methoxyphenyl) propionaldehyde (3.42 g, 19.0 mmol) were added to 80% methanol aqueous solution (200 ml), and the mixture was stirred at 40° C. in a short time. To this solution, 10% palladium carbon in the water content of 50% (1.78 g) was added, and thus obtained mixture was stirred under hydrogen atmosphere of normal pressure (0.1 MPa) at 40° C. for 40 hours. The reaction solution was filtrated to remove the catalyst, and the filtrate was subjected to the high performance liquid chromatography (HPLC) for determination to produce the title compound (6.89 g, 15.0 mmol, 78.9%).

Example 2
Production of N-[N-[3-(3-Hydroxy-4-Methoxyphenyl) Propyl]-L-α-Aspartyl]-L-Phenylalanine 1-Methyl Ester Aspartame (5.89 g, 20.0 mmol) and 3-(3-hydroxy-4-methoxyphenyl) propionaldehyde (3.42 g, 19.0 mmol) were added to methanol (150 ml), and the mixture was stirred in a short time. To thus obtained slurry, 10% palladium carbon in the water content of 50% (1.78 g) was added, and thus obtained mixture was stirred under hydrogen atmosphere of normal pressure (0.1 MPa) at room temperature for 24 hours. The reaction solution was filtrated to remove the catalyst, and the filtrate was subjected to the HPLC for determination to produce the title compound (5.92 g, 12.9 mmol, 67.9%).

Example 3
Production of N-[N-[3-(2-Hydroxy-4-Methoxyphenyl) Propyl]-L-α-Aspartyl]-L-Phenylalanine 1-Methyl Ester Aspartame (5.89 g, 20.0 mmol) and 3-(2-hydroxy-4-methoxyphenyl) propionaldehyde (3.42 g, 19.0 mmol) were added to 80% methanol aqueous solution (200 ml), and the mixture was stirred at 40° C. in a short time. To this solution, 10% palladium carbon in the water content of 50% (1.78 g) was added, and thus obtained mixture was stirred under hydrogen atmosphere of normal pressure (0.1 MPa) at 40° C. for 48 hours. The reaction solution was filtrated to remove the catalyst, and the filtrate was subjected to the HPLC for determination to generate the title compound (6.26 g, 13.7 mmol, 72.1%).

Example 4
Production of N-[N-[3-(3-Hydroxy-4-Methoxyphenyl) Propyl]-L-α-Aspartyl]-L-Phenylalanine 1-Methyl Ester Aspartame (0.40 g, 1.47 mmol) and 3-hydroxy-4-methoxycinnamaldehyde (0.25 g, 1.40 mmol) were added to methanol (13 ml), and the mixture was stirred in a short time. To thus obtained slurry, 10% palladium carbon in the water content of 50% (0.12 g) was added, and thus obtained mixture was stirred under hydrogen atmosphere of normal pressure (0.1 MPa) at room temperature for 24 hours. The reaction solution was filtrated to remove the catalyst, and the filtrate was subjected to the HPLC for determination to generate the title compound (0.21 g, 0.46 mmol, 32.8%).

Example 5
Production of N-[N-[3-(3-Methyl-4-Hydroxyphenyl) Propyl]-L-α-Aspartyl]-L-Phenylalanine 1-Methyl Ester Aspartame (5.89 g, 20.0 mmol) and 3-(3-methyl-4-hydroxyphenyl) propionaldehyde (3.12 g, 19.0 mmol) were added to 60% methanol aqueous solution (150 ml), and the mixture was stirred in a short time. To thus obtained slurry, 10% palladium carbon in the water content of 50% (2.00 g) was added, and thus obtained mixture was stirred under hydrogen atmosphere of normal pressure (0.1 MPa) at room temperature for 48 hours. The reaction solution was filtrated to remove the catalyst, and the filtrate was subjected to the HPLC for determination to generate the title compound (6.92 g, 15.7 mmol, 82.6%).

Example 6
Production of N-[N-[3-(3,4-Methylenedioxyphenyl) Propyl]-L-α-Aspartyl]-L-Phenylalanine 1-Methyl Ester Aspartame (5.89 g, 20.0 mmol) and 3-(3,4-methylenedioxyphenyl) propionaldehyde (3.12 g, 19.0 mmol) were added to 80% methanol aqueous solution, and the mixture was stirred in a short time. To thus obtained slurry, 10% palladium carbon in the water content of 50% (1.78 g) was added, and thus obtained mixture was stirred under hydrogen atmosphere of normal pressure (0.1 MPa) at room temperature for 48 hours. The reaction solution was filtrated to remove the catalyst, and the filtrate was subjected to the HPLC (high performance liquid chromatography) for determination to generate the title compound (6.21 g, 14.0 mmol, 73.7%).

Example 7
Production of N-[N-[3-(4-Hydroxyphenyl) Propyl]-L-α-Aspartyl]-L-Phenylalanine 1-Methyl Ester Aspartame (5.89 g, 20.0 mmol) and 3-(4-hydroxyphenyl) propionaldehyde (2.85 g, 19.0 mmol) were added to 60% methanol aqueous solution (200 ml), and the mixture was stirred at 40° C. in a short time. To this solution, 10% palladium carbon in the water content of 50% (1.78 g) was added, and thus obtained mixture was stirred under hydrogen atmosphere of normal pressure (0.1 MPa) at 40° C. for 48 hours. The reaction solution was filtrated to remove the catalyst, and the filtrate was subjected to the HPLC for determination to produce the title compound (6.18 g, 14.4 mmol, 75.8%).

Example 8
Production of N-[N-[3-(3-Hydroxy-4-Methylphenyl) Propyl]-L-α-Aspartyl]-L-Phenylalanine 1-Methyl Ester Aspartame (5.89 g, 20.0 mmol) and 3-(3-hydroxy-4-methylphenyl) propionaldehyde (3.12 g, 19.0 mmol) were added to 80% methanol aqueous solution (150 ml), and the mixture was stirred in a short time. To thus obtained slurry, 10% palladium carbon in the water content of 50% (1.78 g) was added, and thus obtained mixture was stirred under hydrogen atmosphere of normal pressure (0.1 MPa) at room temperature for 48 hours. The reaction solution was filtrated to remove the catalyst, and the filtrate was subjected to the HPLC for determination to produce the title compound (6.97 g, 15.8 mmol, 83.2%).

Example 9
Production of N-[N-[3-(2-Hydroxy-3-Methoxyphenyl) Propyl]-L-α-Aspartyl]-L-Phenylalanine 1-Methyl Ester Aspartame (5.89 g, 20.0 mmol) and 2-hydroxy-3-methoxycinnamaldehyde [3-(2-hydroxy-3-methoxyphenyl)-2-propenyl aldehyde] (3.38 g, 18.0 mmol) were added to 80% methanol aqueous solution (200 ml), and the mixture was stirred in a short time. To thus obtained slurry, 10% palladium carbon in the water content of 50% (1.78 g) was added, and thus obtained mixture was stirred under hydrogen atmosphere of normal pressure (0.1 MPa) at room temperature for 48 hours. The reaction solution was filtrated to remove the catalyst, and the filtrate was subjected to the HPLC for determination to produce the title compound (4.26 g, 9.3 mmol, 48.9%).

Example 10
Production of N-[N-[3-(3-Hydroxy-4-Methoxyphenyl) Propyl]-L-α-Aspartyl]-L-Phenylalanine 1-Methyl Ester Aspartame (5.89 g, 20.0 mmol) and 3-(3-benzyloxy-4-methoxyphenyl) propionaldehyde (5.15 g, 19.0 mmol) were added to 80% methanol aqueous solution (200 ml), and the mixture was stirred in a short time. To thus obtained slurry, 10% palladium carbon in the water content of 50% was added, and thus obtained mixture was stirred under hydrogen atmosphere of normal pressure (0.1 MPa) at room temperature for 40 hours. The reaction solution was filtrated to remove the catalyst, and the filtrate was subjected to the HPLC for determination to produce the title compound (7.01 g, 15.3 mmol, 80.5%).

Example 11
Production of N-[N-[3-(3-Hydroxy-4-Methoxylphenyl) Propyl]-L-α-Aspartyl]-L-Phenylalanine 1-Methyl Ester Aspartame (5.89 g, 20.0 mmol) and 3-(3-hydroxy-4-methoxyphenyl) propionaldehyde (3.42 g, 19.0 mmol) were added to 80% methanol aqueous solution (180 ml), and further acetic acid (10 ml) was added thereto, and the mixture was stirred in a short time. To thus obtained slurry, 10% palladium carbon in the water content of 50% (1.78 g) was added, and thus obtained mixture was stirred under hydrogen atmosphere of normal pressure (0.1 MPa) at room temperature for 24 hours. The reaction solution was filtrated to remove the catalyst, and the filtrate was subjected to the HPLC for determination to produce the title compound (6.72 g, 14.7 mmol, 77.4%).

Example 12
Production of N-[N-[3-(2,4-Dihydroxyphenyl) Propyl]-L-α-Aspartyl]-L-Phenylalanine 1-Methyl Ester Aspartame (5.89 g, 20.0 mmol) and 3-(2,4-dihydroxyphenyl) propionaldehyde (3.15 g, 19.0 mmol) were added to 80% methanol aqueous solution (200 ml), and the mixture was stirred in a short time. To thus obtained slurry, 10% palladium carbon in the water content of 50% was added, and thus obtained mixture was stirred under hydrogen atmosphere of normal pressure (0.1 MPa) at room temperature for 40 hours. The reaction solution was filtrated to remove the catalyst, and the filtrate was subjected to the HPLC for determination to produce the title compound (5.94 g, 13.4 mmol, 70.5%).

Example 13
Production of 3-Hydroxy-4-Methoxycinnamaldehyde

In a chemical reactor for hydrogen addition (hydrogenation) under elevated pressure, previously tetrahydrofuran (64 ml) was bubbled with nitrogen gas for 10 minutes.

Palladium acetate (58 mg, 0.257 mmol), tri(p-tolyl) phosphine (157 mg, 0.515 mmol), 3-hydroxy-4-methoxycinnamic acid (5.00 g, 25.7 mmol) and pivalic acid anhydride (14.4 g, 77.2 mmol) were added thereto, and thereafter the mixture was bubbled with nitrogen gas for 30 minutes to substitute nitrogen gas completely for the gas in the system of reaction, whereby the system was filled with nitrogen gas. Next, hydrogen gas was added thereinto to substitute hydrogen gas for the gas in the system, and then the mixture was stirred under hydrogen pressure of 3.4 MPa at 80° C. for 24 hours for reaction. Thus obtained reaction solution was concentrated under reduced pressure to remove tetrahydrofuran by vaporization. The remaining residue was subjected to a purification process with a silica gel column chromatography (eluting solvent: toluene/ethyl acetate=4/1) to obtain 3-hydroxy-4-methoxycinnamaldehyde (2.26 g, 12.7 mmol, yield: 49%).

Example 14
Production of 3-(3-Hydroxy-4-Methoxylphenyl) Propionic Acid

3-Hydroxy-4-methoxycinnamic acid (15.0 g, 77.2 mmo) and 10% palladium carbon in the water content of 50% (2.26 g) were added to a mixed solvent (330 ml) of methanol and water (mixing ratio of 10:1 v/v), and the mixture was stirred under hydrogen atmosphere of normal pressure (0.1 MPa) at 50° C. for 5 hours for reaction. The reaction solution was filtrated to remove the catalyst, and the filtrate was concentrated under reduced pressure to solidification to obtain 3-(3-hydroxy-4-methoxyphenyl) propionic acid (15.1 g, 76.7 mmol, yield: 99%).

Example 15
Production of 3-(3-Hydroxy-4-Methoxyphenyl) Propionaldehyde

3-Hydroxy-4-methoxycinnamaldehyde (8.66 g, 48.6 mmol) and 5% palladium-alumina (aluminum oxide) (0.540 g) were added to methanol (144 ml), and the mixture was stirred under hydrogen atmosphere of normal pressure (0.1 MPa) at 35° C. for 7 hours for reaction. The reaction solution was filtrated to remove the catalyst, and further the catalyst was washed with methanol (40 ml). The filtrate and the wash solution were combined together, and then concentrated. Thus concentrated solution was subjected to a purification process with a silica gel column chromatography (eluting solvent: toluene/ethyl acetate=4/1). The thus eluted fractions containing the object compound were concentrated under reduced pressure to obtain crude 3-(3-hydroxy-4-methoxyphenyl) propionaldehyde (6.86 g, 38.1 mmol, yield: 78%) in the slightly yellow coloured solid.

Thus obtained crude 3-(3-hydroxy-4-methoxyphenyl) propionaldehyde was recrystallized from toluene to obtain purified 3-(3-hydroxy-4-methoxyphenyl) propionaldehyde (5.83 g, 32.3 mmol, crystallization yield: 85%) in the white crystalline form.

Example 16
Production of 3-(3-Hydroxy-4-Methoxyphenyl) Propionaldehyde

Into a chemical reactor for hydrogen addition (hydrogenation) under elevated pressure, 3-(3-hydroxy-4-methoxyphenyl) propionic acid (5.09 g, 25.9 mmol), pivalic acid anhydride (14.3 g, 76.6 mmol), and tetrahydrofuran (64 ml) were added, and thereafter the mixture was bubbled with nitrogen gas for 10 minutes. Palladium acetate (57 mg, 0.254 mmol) and triphenylphosphine (349 mg, 1.33 mmol) were added thereto, and thereafter the mixture was bubbled with nitrogen gas for 20 minutes to substitute nitrogen gas completely for the gas in the system of reaction, whereby the system was filled with nitrogen gas. Next, hydrogen gas was added thereinto to substitute hydrogen gas for the gas in the system, and then the mixture was stirred under hydrogen pressure of 5.4 MPa at 80° C. for 24 hours for reaction. Thus obtained reaction solution was concentrated under reduced pressure to remove tetrahydrofuran by vaporization. The remaining residue was subjected to a purification process with a silica gel column chromatography (eluting solvent: hexane/ethyl acetate=2/1). The thus eluted fractions containing the object compound were concentrated under reduced pressure to obtain crude 3-(3-hydroxy-4-methoxyphenyl) propionaldehyde (2.26 g, 12.5 mmol, yield: 48%) in the slightly yellow coloured solid.

Thus obtained crude 3-(3-hydroxy-4-methoxyphenyl) propionaldehyde was recrystallized from toluene to obtain purified 3-(3-hydroxy-4-methoxyphenyl) propionaldehyde (1.94 g, 10.8 mmol, crystallization yield: 86%) in the white crystalline form.

Example 17
Physical Properties on 3-(3-Hydroxy-4-Methoxyphenyl) Propionaldehyde The physical properties on the title compound obtained in the present invention were in the followings.

White Crystals
(Differential Thermal Analysis)
Temperature range for the determination: 50–300° C.; Heating-up speed: 10° C./minute; Melting point: 71° C.
$^1$H—NMR (CDCl$_3$):
δ: 2.70–2.75 (m, 2H), 2.84–2.89 (m, 2H), 3.86 (s, 3H), 5.64 (s, 1H), 6.64–6.68 (m, 1H), 6.75–6.78 (m, 2H), 9.80 (t, J=1.5 Hz, 1H).
ESI-MS:
Calculation: C$_{10}$H$_{12}$O$_3$=180.2, Analysis: 179.2(MH$^-$).

Example 18
Production of N-[N-[3-(3-Hydroxy-4-Methoxyphenyl) Propyl]-L-α-Aspartyl]-L-Phenylalanine 1-Methyl Ester 3-(3-Hydroxy-4-methoxyphenyl) propionaldehyde (1.50 g, 8.32 mmol) and aspartame (2.57 g, 8.74 mmol) were added to a mixed solvent (86 ml) of methanol and water (Mixing ratio of 4:1 v/v), and 10% palladium carbon in the water content of 50% (0.77 g) was added thereto. The mixture was stirred under hydrogen atmosphere of normal pressure (0.1 MPa) at 35° C. for 48 hours for reaction. After completion of the reaction, the catalyst was removed by filtration and further washed with methanol (20 ml). The filtrate and the wash solution were combined together, and subjected to the high performance liquid chromatography (HPLC) for determination to generate N-[N-[3-(3-hydroxy-4-methoxyphenyl) propyl]-L-α-aspartyl]-L-phenylalanine 1-methyl ester (2.69 g, 5.87 mmol, yield: 71%).

Data on the NMR spectrum and mass spectrum of N-[N-[3-(3-hydroxy-4-methoxyphenyl) propyl]-L-α-aspartyl]-L-phenylalanine 1-methyl ester are shown in the followings.
$^1$H—NMR (DMSO-d6):
δ: 1.50–1.60 (m, 2H), 2.15–2.40 (m, 6H), 2.87–2.97 (dd, 1H), 3.05–3.13 (dd, 1H), 3.37–3.43 (m, 1H), 3.62 (s, 3H), 3.71 (s, 3H), 4.50–4.60 (m, 1H), 6.52 (d, 1H), 6.60 (s, 1H), 6.79 (d, 1H), 7.18–7.30 (m, 5H), 8.52 (d, 1H), 8.80 (brs, 1H).
ESI-MS:
Calculation: C$_{24}$H$_{30}$N$_2$O$_7$=458.5, Analysis: 459.2(MH$^+$).

Effect of Invention

According to the present invention, a N-[N-[3-(phenyl with substituent group(s)) propyl]-L-α-aspartyl]-L-phenylalanine 1-methyl ester expected to serve as a sweetener, can be produced industrially and efficiently.

Further, according to the present invention, a cinnamaldehyde derivative derivative and a hydrocinnamaldehyde derivative useful as intermediates for the production of the above N-[N-[3-(phenyl with substituent group(s)) propyl]-L-α-aspartyl]-L-phenylalanine 1-methyl ester, can be produced industrially and efficiently.

In addition, by using a 3-(3-hydroxy-4-methoxyphenyl) propionaldehyde which is a novel arylpropionaldehyde used desirably as an intermediate for the production in the present invention, a N-[N-[3-(3-hydroxy-4-methoxyphenyl) propyl]-L-α-aspartyl]-L-phenylalanine 1-methyl ester particularly useful as a sweetener having a high sweetening potency can be produced industrially and efficiently.

The above arylpropionaldehyde is a novel compound, and it can be produced easily and efficiently based on the process for using a 3-hydroxy-4-methoxycinnamic acid as the starting material,
converting the carboxyl group in the compound into a formyl group, and then reducing the carbon—carbon double bond therein selectively, or
reducing the carbon—carbon double bond in the compound selectively, and then converting the carboxyl group therein into a formyl group.

As explained above, according to the process in the present invention, a N-[N-[3-(3-hydroxy-4-methoxyphenyl) propyl]-L-α-aspartyl]-L-phenylalanine 1-methyl ester which is a particularly useful sweetener having a high sweetening potency, can be produced industrially and advantageously.

The present application claims priority to JP11-287398, which was filed on Oct. 7, 1999 and JP11-37128, which was filed on Dec. 27, 1999, and are incorporated herein by reference.

What is claimed is:
1. A process for producing a compound of formula (3):

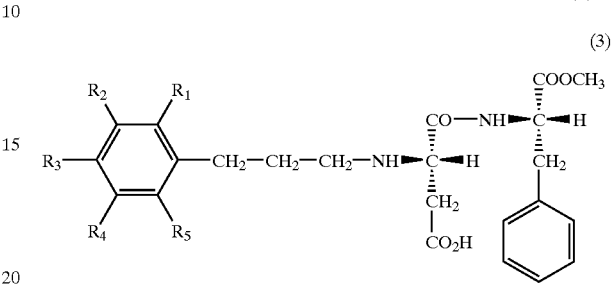

wherein $R_1$, $R_2$, $R_3$, $R_4$, and $R_5$ are independently selected from the group consisting of a hydrogen atom, a hydroxyl group, an alkoxy group having 1 to 3 carbon atoms, an alkyl group having 1 to 3 carbon atoms, and a hydroxyalkyloxy group having 2 or 3 carbon atoms, wherein said process comprises:

(a) converting a carboxyl group in a compound of formula (4) into a formyl group:

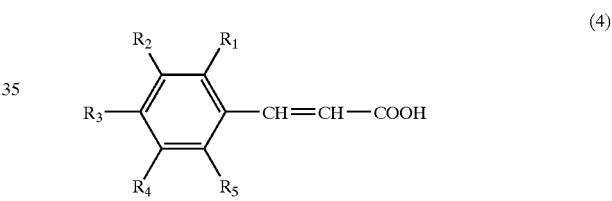

wherein $R_1$, $R_2$, $R_3$, $R_4$, and $R_5$ are as defined above, to obtain a compound of formula (2):

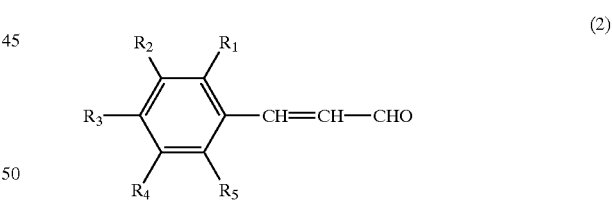

wherein $R_1$, $R_2$, $R_3$, $R_4$, and $R_5$ are defined as above; and (b) reductively alkylating aspartame with said compound of formula (2) and hydrogen in the presence of catalyst, to obtain said compound of formula (3).

2. The process of claim 1, wherein $R_2$ is a hydroxyl group, $R_3$ is a methoxy group, and $R_1$, $R_4$, and $R_5$ are hydrogen atoms.

3. The process of claim 1, wherein said catalyst is selected from the group consisting of palladium carbon, platinum carbon, and mixtures thereof.

4. The process of claim 1, wherein said reductively alkylating is performed in a solvent which is selected from the group consisting of methanol, water, and mixtures thereof.

5. A process for producing a compound of formula (3):

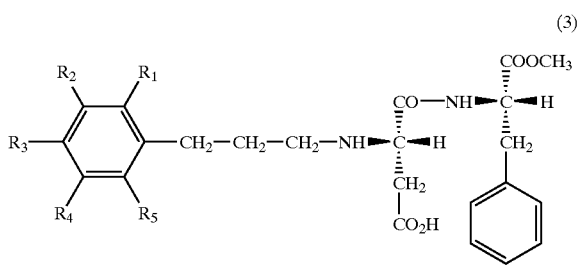

wherein $R_1$, $R_2$, $R_3$, $R_4$, and $R_5$ are independently selected from the group consisting of a hydrogen atom, a hydroxyl group, an alkoxy group having 1 to 3 carbon atoms, an alkyl group having 1 to 3 carbon atoms, and a hydroxyalkyloxy group having 2 or 3 carbon atoms, wherein said process comprises:

(a) reducing a double bond in a compound of formula (2):

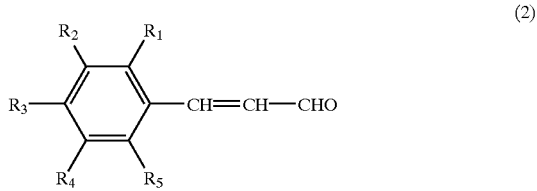

wherein $R_1$, $R_2$, $R_3$, $R_4$, and $R_5$ are as defined above, to obtain a compound of formula (1):

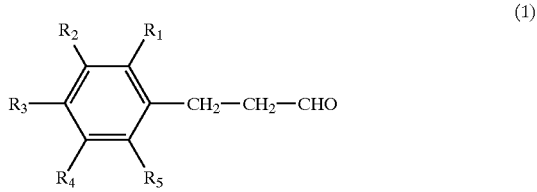

wherein $R_1$, $R_2$, $R_3$, $R_4$, and $R_5$ are defined as above; and (b) reductively alkylating aspartame with said compound of formula (1) and hydrogen in the presence of catalyst, to obtain said compound of formula (3).

6. The process of claim 5, wherein $R_2$ is a hydroxyl group, $R_3$ is a methoxy group, and $R_1$, $R_4$, and $R_5$ are hydrogen atoms.

7. The process of claim 5, wherein said catalyst is selected from the group consisting of palladium carbon, platinum carbon, and mixtures thereof.

8. The process of claim 5, wherein said reductively alkylating is performed in a solvent which is selected from the group consisting of methanol, water, and mixtures thereof.

9. A process for producing a compound of formula (3):

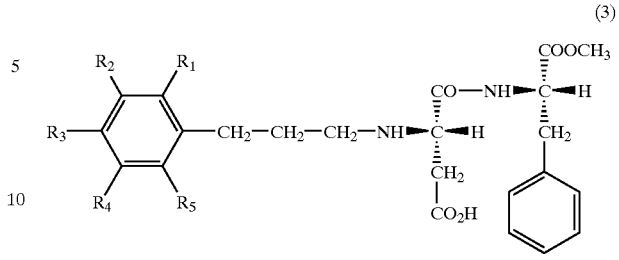

wherein $R_1$, $R_2$, $R_3$, $R_4$, and $R_5$ are independently selected from the group consisting of a hydrogen atom, a hydroxyl group, an alkoxy group having 1 to 3 carbon atoms, an alkyl group having 1 to 3 carbon atoms, and a hydroxyalkyloxy group having 2 or 3 carbon atoms, wherein said process comprises:

(a) converting a carboxyl group in a compound of formula (4) into a formyl group:

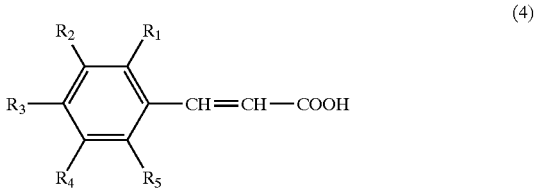

wherein $R_1$, $R_2$, $R_3$, $R_4$, and $R_5$ are as defined above, to obtain a compound of formula (2):

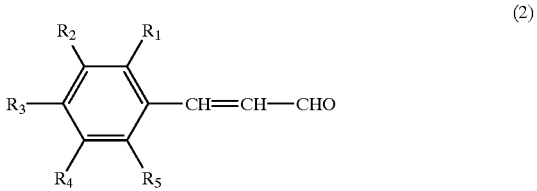

wherein $R_1$, $R_2$, $R_3$, $R_4$, and $R_5$ are defined as above;

(b) reducing a double bond in said compound of formula (2), to obtain a compound of formula (1):

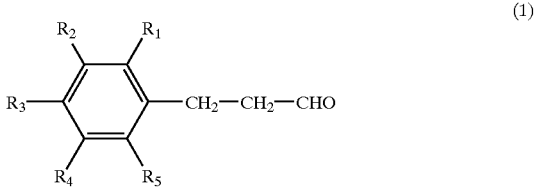

wherein $R_1$, $R_2$, $R_3$, $R_4$, and $R_5$ are defined as above; and (c) reductively alkylating aspartame with said compound of formula (1) and hydrogen in the presence of catalyst, to obtain said compound of formula (3).

10. The process of claim 9, wherein $R_2$ is a hydroxyl group, $R_3$ is a methoxy group, and $R_1$, $R_4$, and $R_5$ are hydrogen atoms.

11. The process of claim 9, wherein said catalyst is selected from the group consisting of palladium carbon, platinum carbon, and mixtures thereof.

12. The process of claim 9, wherein said reductively alkylating is performed in a solvent which is selected from the group consisting of methanol, water, and mixtures thereof.

13. A process for producing a compound of formula (3):

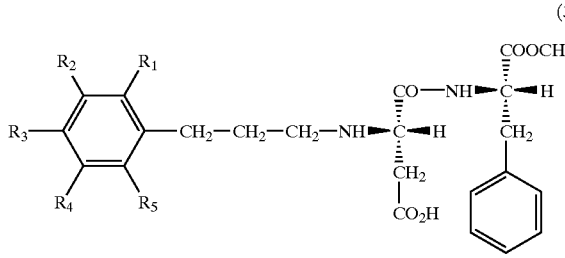

(3)

wherein $R_1$, $R_2$, $R_3$, $R_4$, and $R_5$ are independently selected from the group consisting of a hydrogen atom, a hydroxyl group, an alkoxy group having 1 to 3 carbon atoms, an alkyl group having 1 to 3 carbon atoms, and a hydroxyalkyloxy group having 2 or 3 carbon atoms, wherein said process comprises:

(a) converting a carboxyl group in a compound of formula (5) into a formyl group:

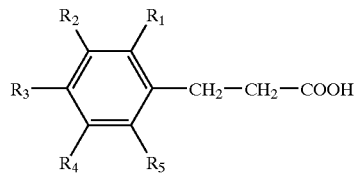

(5)

wherein $R_1$, $R_2$, $R_3$, $R_4$, and $R_5$ are as defined above, to obtain a compound of formula (1):

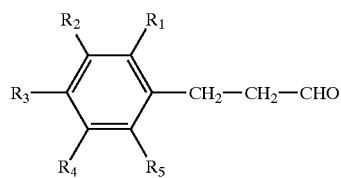

(1)

wherein $R_1$, $R_2$, $R_3$, $R_4$, and $R_5$ are defined as above; and (b) reductively alkylating aspartame with said compound of formula (1) and hydrogen in the presence of catalyst, to obtain said compound of formula (3).

14. The process of claim 13, wherein $R_2$ is a hydroxyl group, $R_3$ is a methoxy group, and $R_1$, $R_4$, and $R_5$ are hydrogen atoms.

15. The process of claim 13, wherein said catalyst is selected from the group consisting of palladium carbon, platinum carbon, and mixtures thereof.

16. The process of claim 13, wherein said reductive alkylating is performed in a solvent which is selected from the group consisting of methanol, water, and mixtures thereof.

17. A process for producing a compound of formula (3):

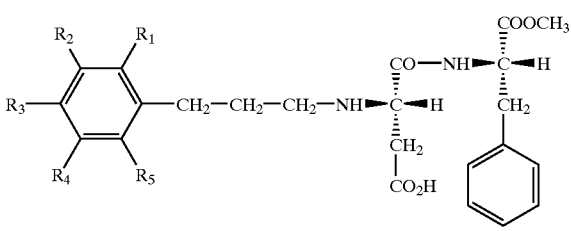

(3)

wherein $R_1$, $R_2$, $R_3$, $R_4$, and $R_5$ are independently selected from the group consisting of a hydrogen atom, a hydroxyl group, an alkoxy group having 1 to 3 carbon atoms, an alkyl group having 1 to 3 carbon atoms, and a hydroxyalkyloxy group having 2 or 3 carbon atoms, wherein said process comprises:

(a) reducing a double bond in a compound of formula (4):

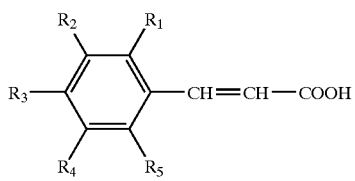

(4)

wherein $R_1$, $R_2$, $R_3$, $R_4$, and $R_5$ are as defined above, to obtain a compound of formula (5):

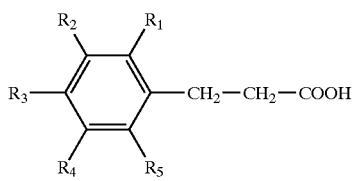

(5)

wherein $R_1$, $R_2$, $R_3$, $R_4$, and $R_5$ are defined as above;

(b) converting a carboxyl group in said compound of formula (5) into a formyl group, to obtain a compound of formula (1):

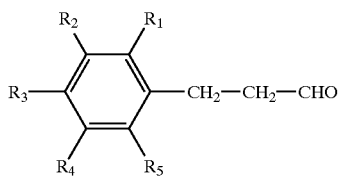

(1)

wherein $R_1$, $R_2$, $R_3$, $R_4$, and $R_5$ are defined as above; and (c) reductively alkylating aspartame with said compound of formula (1) and hydrogen in the presence of catalyst, to obtain said compound of formula (3).

18. The process of claim 17, wherein $R_2$ is a hydroxyl group, $R_3$ is a methoxy group, and $R_1$, $R_4$, and $R_5$ are hydrogen atoms.

19. The process of claim 17, wherein said catalyst is selected from the group consisting of palladium carbon, platinum carbon, and mixtures thereof.

20. The process of claim 17, wherein said reductively alkylating is performed in a solvent which is selected from the group consisting of methanol, water, and mixtures thereof.

* * * * *